United States Patent
Moinet et al.

(10) Patent No.: US 6,518,458 B1
(45) Date of Patent: Feb. 11, 2003

(54) (AMINOIMINOMETHYL) AMINO) ALKANE-CARBOXAMIDES AND THEIR APPLICATIONS IN THERAPY

(75) Inventors: Gérard Moinet, Orsay (FR); Daniel Cravo, Sartrouville (FR); Didier Mesangeau, Combs la Ville (FR); Liliane Doare, Viry Chatillon (FR); Micheline Kergoat, Bures sur Yvette (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/869,957

(22) PCT Filed: Dec. 30, 1999

(86) PCT No.: PCT/EP99/10468

§ 371 (c)(1),
(2), (4) Date: Jul. 10, 2001

(87) PCT Pub. No.: WO00/42001

PCT Pub. Date: Jul. 20, 2000

(30) Foreign Application Priority Data

Jan. 11, 1999 (FR) .............................. 99 00194

(51) Int. Cl.[7] ..................... C07C 233/05; C07C 231/12; A61K 31/16

(52) U.S. Cl. ..................... 564/194; 564/193; 564/196; 546/296; 514/378; 514/626

(58) Field of Search ................... 564/193, 194, 564/196; 546/296; 514/626, 348

(56) References Cited

U.S. PATENT DOCUMENTS 6,147,258 A * 11/2000 Greindl et al. .............. 562/560

FOREIGN PATENT DOCUMENTS

GB    1153424    5/1969

OTHER PUBLICATIONS

Breaux E J Et Al: "An improved general synthesis of 4–aryl–5–pyrimidinecarboxylates" J. Heterocycl. Chem. (JHTCAD, 0022152X); 1981; vol. 18,; pp. 183–4, XP002117468 Monsanto Agric. Products Co.;Res. Dep.; St. Louis; 63166; MO.

Patent Abstracts of Japan vol. 1996, No. –A, Jun. 28, 1996 & JP 08 041008 A (Ono Pharmace UT CO LTD), Feb. 13, 1996.

R. Panicucci Et Al.: "4,5–Dihydro–4,5–dihydroxyimidazoles as products of the reduction of 2–nitroimidazoles, Hplc assay and demaonstration of equilibrium trasfer of glyoxal to guanine" Canadian Journal of Chemistry., vol. 67, 1989, pp. 2128–2135, XP002117469 National Research Council. Ottawa., CA ISSN: 0008–4042.

Guillou Y Et Al: "Phascoline[377N–(3–guanidinopropionyl)–2–hyd roxy-n–heptylamine 377]and phascolosomine [377N–(3–guanidinoisobutyryl)–2–methoxy-n–heptylamine 377], two new guanidino compounds from sipunculid worms. Isolation and structure" J. Biol. Chem. (JBCHA3); 1973; vol.248 (16); pp. 5668–72, XP002117857 Coll. France;Ec. Prat. Hautes Etud.; Paris; Fr.

Yokoi, Isao Et Al: "Relationship between structure and inhibitory effect of arginine analogs on neuronal nitric oxide synthase activity" Neurochem. Res. (1996), 21(10), 1187–1192, 1996, XP002135433.

* cited by examiner

Primary Examiner—Shailendra Kumar
(74) Attorney, Agent, or Firm—Millen, White, Zelano & Branigan, P.C.

(57) ABSTRACT

The invention to a pharmaceutical composition comprising as active principle a compound of general formula (I), in which $R_1$, $R_2$, $R_3$, and A are as defined in claim 1. These compositions can be used in the treatment of pathologies associated with insulin resistance syndrome.

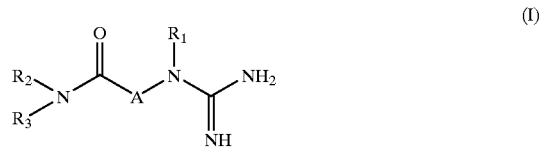

(I)

4 Claims, No Drawings

(AMINOIMINOMETHYL) AMINO) ALKANE-CARBOXAMIDES AND THEIR APPLICATIONS IN THERAPY

This application is a 371 of PCT/EP99/10468, filed Dec. 30, 1999.

The present invention relates to the use of derivatives of the ((aminoiminomethyl)amino)alkane-carboxamide type in the treatment of pathologies associated with insulin resistance syndrome.

The present invention therefore provides pharmaceutical compositions comprising as active principle a compound of general formula (I)

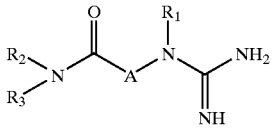

in which:
$R_1$ is selected from one of the following groups:
  H;
  $(C_1-C_{20})$alkyl substituted or unsubstituted by one or more of the following groups:
    amino, hydroxyl, $(C_1-C_5)$alkyl, $(C_1-C_5)$alkoxy, $(C_1-C_5)$alkylthio, $(C_1-C_5)$alkylamino, trifluoromethyl;
$R_2$ and $R_3$ are selected independently from
  H;
  $(C_3-C_8)$cycloalkyl substituted or unsubstituted by one or more of the following groups:
    amino, hydroxyl, $(C_1-C_5)$ alkyl, $(C_1-C_5)$ alkoxy, $(C_1-C_5)$alkylthio, $(C_1-C_5)$alkylamino, trifluoromethyl;
  $(C_3-C_8)$heterocycloalkyl containing one or more heteroatoms selected from N, O and S and substituted or unsubstituted by one or more of the following groups:
    amino, hydroxyl, $(C_1-C_5)$alkyl, $(C_1-C_5)$alkoxy, $(C_1-C_5)$alkylthio, $(C_1-C_5)$alkylamino, trifluoromethyl; a nitrogen atom can additionally be substituted by a $(C_6-C_{14})$ aryl, $(C_6-C_{14})$ acyl or $(C_1-C_5)$ alkyl group;
  $(C_6-C_{14})$aryl substituted or unsubstituted by one or more of the following groups:
    amino, hydroxyl, halogen, $(C_1-C_5)$alkyl, $(C_1-C_5)$ alkoxy, $(C_1-C_5)$ alkylthio, $(C_1-C_5)$ alkylamino, trifluoromethyl, cyano;
  $(C_1-C_{13})$heteroaryl containing one or more heteroatoms selected from N, O and S and substituted or unsubstituted by one or more of the following groups:
    amino, hydroxyl, halogen, $(C_1-C_5)$alkyl, $(C_1-C_5)$ alkoxy, $(C_1-C_5)$alkylthio, $(C_1-C_5)$ alkylamino, trifluoromethyl, cyano; a nitrogen atom can additionally be substituted by a $(C_6-C_{14})$aryl, $(C_6-C_{14})$acyl or $(C_1-C_5)$ alkyl group;
  $(C_6-C_{14})$aryl-$(C_1-C_5)$alkyl substituted or unsubstituted by one or more of the following groups:
    amino, hydroxyl, halogen, $(C_1-C_5)$alkyl, $(C_1-C_5)$ alkoxy, $(C_1-C_5)$alkylthio, $(C_1-C_5)$alkylamino, trifluoromethyl, cyano;
and A is selected from the groups:
  —$CH_2$—,
  —$CH_2$—$CH_2$—,
  —$CHR_4$—,

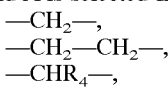

$R_4$ being selected from:
  H;
  $(C_1-C_{20})$ alkyl substituted or unsubstituted by one or more of the following groups:
    amino, hydroxyl, $(C_1-C_5)$alkyl, $(C_1-C_5)$alkoxy, $(C_1-C_5)$alkylthio, $(C_1-C_5)$alkylamino, trifluoromethyl;
  $(C_3-C_8)$cycloalkyl substituted or unsubstituted by one or more of the following groups:
    amino, hydroxyl, $(C_1-C_5)$ alkyl, $(C_1-C_5)$ alkoxy, $(C_1-C_5)$alkylthio, $(C_1-C_5)$alkylamino, trifluoromethyl;
  $(C_3-C_8)$ heterocycloalkyl containing one or more heteroatoms selected from N, O and S and substituted or unsubstituted by one or more of the following groups:
    amino, hydroxyl, $(C_1-C_5)$ alkyl, $(C_1-C_5)$ alkoxy, $(C_1-C_5)$alkylthio, $(C_1-C_5)$ alkylamino, trifluoromethyl; a nitrogen atom can additionally be substituted by a $(C_6-C_{14})$ aryl, $(C_6-C_{14})$ acyl or $(C_1-C_5)$ alkyl group;
and their solvates and pharmaceutically acceptable salts.

The heteroaryl groups are selected in particular from pyridyl, pyrimidinyl, furyl, pyrrolyl, thienyl, benzothiazolyl, benzoxazolyl, benzimidazolyl, benzothienyl, indolyl, benzofuryl and imidazolyl.

The heterocycloalkyl groups are selected in particular from piperidinyl, morpholinyl, piperazinyl, tetrahydrofuryl, tetrahydrothienyl, pyrrolidinyl and tetrahydropyranyl.

A preferred group of compounds of formula I is constituted in which $R_1$ is H or $(C_1-C_6)$alkyl.

A preferred group of compounds of formula I is constituted in which:
$R_2$ is selected from
  $(C_3-C_8)$ cycloalkyl substitued or unsubstituted by one or more of the following groups: amino, hydroxyl, $(C_1-C_5)$ alkyl, $(C_1-C_5)$alkoxy, $(C_1-C_5)$alkylthio, $(C_1-C_5)$alkylamino, trifluoromethyl;
  $(C_6-C_{14})$ aryl substituted or unsubstituted by one or more of the following groups: amino, hydroxyl, halogen, $(C_1-C_5)$ alkyl, $(C_1-C_5)$alkoxy, $(C_1-C_5)$ alkylthio, $(C_1-C_5)$alkylamino, trifluoromethyl, cyano;
  $(C_1-C_{13})$ heteroaryl containing one or more heteroatoms selected from N, O and S and substituted or unsubstituted by one or more of the following groups: amino, hydroxyl, halogen, $(C_1-C_5)$ alkyl, $(C_1-C_5)$ alkoxy, $(C_1-C_5)$alkylthio, $(C_1-C_5)$ alkylamino, trifluoromethyl, cyano;
a nitrogen atom can additionally be substituted by a $(C_6-C_{14})$ aryl, $(C_6-C_{14})$ acyl or $(C_1-C_5)$ alkyl group.

A particularly preferred group of compounds of formula I is constituted in which $R_2$ is selected from a $(C_6-C_{14})$ aryl group possibly substituted as defined above.

To the knowledge of the Applicant, the compounds of formula (I) are novel with the exception of α-guanidinoacetanilide, which is described by Mazundar (Indian Drugs 1989, 27, 5, 292), i.e. the compound of formula I in which R=H, $R_2$=phenyl and $R_3$=H.

The invention also relates to the tautomeric forms, to the enantiomers, diastereoisomers and epimers of the compounds of general formula (I).

The compounds of general formula (I) have basic nitrogen atoms and can be monosalified or disalified by mineral or organic acids.

The compounds of formula (I) can be prepared by reacting a compound of formula:

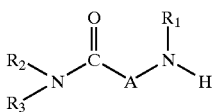

with a compound of formula:

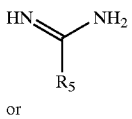

or

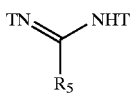

in which:

R$_5$ is selected from —SCH$_3$, pyrazolyl or —SO$_3$H, and

T is a tert-butyloxycarbonyl or benzyloxycarbonyl protective group.

The compounds of formula (II) can be prepared in accordance with a process in which:

a) a compound of formula:

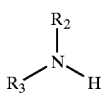

in which R$_2$ and R$_3$ are as defined above is reacted with an acyl halide of general formula (VI):

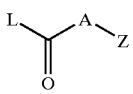

in which:

A is as defined above,

L represents a chlorine or bromine atom or an activated ester form,

Z represents a chlorine or bromine atom or a protected amino group, to form a compound of general formula (VII):

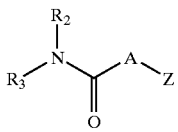

in which R$_2$, R$_3$, A and Z are as defined above;

b) the compound of general formula (VII) is reacted with potassium phthalimide and then with hydrazine monohydrate or else with a nitride followed by a reduction to form a compound of general formula (II) in which R$_1$=H.

In the case where Z is a protected amino group, it is appropriate to deprotect it at this stage to form a compound of general formula (II).

The compounds of general formula (II) in which R$_1$ is other than H can be obtained by reacting a compound of formula (VII) with an amine of general formula (VIII):

$$R_1NH_2 \qquad (VIII).$$

The compositions according to the present invention are useful in the treatment of pathologies associated with insulin resistance syndrome (syndrome X).

Insulin resistance is characterized by a reduction in the action of insulin (cf. Presse Medicale, 1997, 26 (No. 14), 671–677) and is involved in a large number of pathological states, such as diabetes and, more particularly, non-insulin-dependent diabetes (type II diabetes or NIDDM), dyslipidaemia, obesity, arterial hypertension, and certain microvascular and macrovascular complications such as atherosclerosis, retinopathies and neuropathies.

In this context, reference may be made, for example, to Diabetes, Vol. 37, 1988, 1595–1607; Journal of Diabetes and its complications, 1998, 12, 110–119, or Horm. Res., 1992, 38, 28–32.

In particular, the compositions of the invention exhibit a strong hypoglycaemic activity.

The compositions according to the present invention can also be used for treating the chronic complications due to the formation of "advanced glycosylation end products", written AGEs, which result from the glycoxidation reaction between glucose, its oxidation derivatives and the amino functions of proteins, including the so-called Maillard reactions of glycation of glyoxal for example.

The pharmaceutical compositions according to the invention can be provided in forms which are intended for parenteral, oral, rectal, permucous or percutaneous administration.

They will therefore be provided in the form of solutions or suspensions for injection or multi-dose bottles, in the form of plain or coated tablets, film-coated tablets, wafer capsules, gelatin capsules, pills, cachets, powders, suppositories or rectal capsules, or solutions or suspensions for percutaneous use in a polar solvent or for permucous use.

The excipients which are suitable for such administrations are derivatives of cellulose or microcrystalline cellulose, alkaline earth metal carbonates, magnesium phosphate, starches, modified starches, and lactose for the solid forms.

For rectal use, cocoa butter or polyethylene glycol stearates are the preferred excipients.

For parenteral use, water, aqueous solutions, physiological saline and isotonic solutions are the vehicles used most judiciously.

The dosage can vary within wide limits (from 0.5 mg to 1000 mg) depending on the therapeutic indication and the administration route, and also on the age and weight of the individual.

The following examples illustrate the preparation of the compounds of formula (I) and of various intermediates.

A—PREPARATION EXAMPLE OF COMPOUNDS OF FORMULA (VII)

Preparation of N-(2,6-Dimethylphenyl)-3-chloropropanamide

A 2 l three-necked flask, is charged with 121.8 g of 2,6-dimethylaniline, 300 ml of isopropyl ether and 150 ml of water. 126.5 g of 3-chloropropanoyl chloride are added at a rate such that the internal temperature is between 5 and 10°

C. At the end of the addition, the reaction medium is stirred for 3 h. The precipitate formed is filtered off with suction, washed with isopropyl ether and then with water and finally dried. 126 g of white crystals are obtained.

m.p.=134–136° C. $^1$H NMR (DMSO-d6, 200 MHz): 2.18 (s,6H); 2.81 (t,2H); 3.88 (t,2H); 7.03 (d,3H); 9.40 (s,1H).

The formulae and characteristics of compounds of formula (VII) have been collated in Table 1.

TABLE 1

| Compound | Structure | m.p. in ° C. (Kofler) | $^1$H NMR 200 MHz δ ppm |
|---|---|---|---|
| 1 | (2,6-dimethylphenyl)-NH-CO-CH$_2$-Cl | 146–148 lit.: 146–148 | DMSO-d6 2.25 (s,6H) 4.35 (s,2H) 9.10 (s,3H) 9.62 (s,1H) |
| 2 | (2,6-diisopropylphenyl)-NH-CO-CH$_2$-Cl | 148–150 lit.: 151.4–151.9 | cDCl3 1.20 (d,12H) 3.00 (m,2H) 4.20 (s,2H) 7.20 (m,3H) 7.82 (s,1H) |
| 3 | 4-(methylthio)-6-methyl-2-(methylthio)pyridin-3-yl-NH-CO-CH$_2$-Cl | 197–199 lit.: 190–192 | DMSO-d6 2.65 (2s,9H) 4.50 (s,2H) 7.13 (s,1H) 10.06 (s,1H) |
| 4 | (2,6-dimethylphenyl)-NH-CO-CH$_2$-CH$_2$-Cl | 134–136 lit.: 134–136 | DMSO-d6 2.18 (s,6H) 2.81 (t,2H) 3.88 (t,2H) 7.03 (d,3H) 9.40 (s,1H) |
| 5 | (2,6-dimethylphenyl)-NH-CO-CH(CH$_3$)-NH-CO-O-CH$_2$-C$_6$H$_5$ | 176–178 | DMSO-d6 1.23 (d,3H) 2 (s,6H) 4.15 (m,1H) 4.90 (s,2H) 6.90 (s,3H) 7.23 (s,5H) 7.45 (d,1H) 9.20 (s,1H) |
| 6 | (2,4,6-trimethylphenyl)-NH-CO-CH$_2$-Cl | 184–186 | DMSO-d6 2.20 (s,6H) 2.40 (s,3H) 4.35 (s,2H) 7.00 (s,2H) 9.62 (s,1H) |
| 7 | (2,6-dimethylphenyl)-NH-CO-CH(CH(CH$_3$)CH$_2$CH$_3$)-NH-CO-O-CH$_2$-C$_6$H$_5$ | 195–197 | DMSO-d6 1.0 (t,3H) 1.18 (d,3H) 1.25–2.00 (m,3H) 2.30 (s,6H) 4.20 (t,1H) 7.20 (s,3H) 7.50 (s,5H) 7.70 (d,2H) 9.55 (s,1H) |

TABLE 1-continued

| # | Structure | m.p. (°C) | NMR |
|---|---|---|---|
| 8 | (2,6-dimethylphenyl)-NH-C(O)-CH(CH₂CH(CH₃)₂)-NH-C(O)-O-CH₂-phenyl | oil | DMSO-d6<br>1.0 (t,6H)<br>1.69 (m,3H)<br>2.18 (s,6H)<br>4.30 (q,1H)<br>5.09 (q,2H)<br>7.09 (s,3H)<br>7.40 (s,5H)<br>7.63 (d,1H)<br>9.40 (s,1H) |
| 9 | (2,6-dimethylphenyl)-NH-C(O)-CH(CH(CH₃)₂)-NH-C(O)-O-CH₂-phenyl | 210–212 | DMSO-d6<br>1.0 (t,6H)<br>1.70 (m,1H)<br>2.13 (s,6H)<br>4.10 (t,1H)<br>5.11 (q,2H)<br>7.05 (s,3H)<br>7.36 (s,5H)<br>7.50 (d,1H)<br>9.40 (s,1H) |
| 10 | (PhCH₂)₂N-C(O)-CH₂Cl | oil | DMSO-d6<br>4.30 (s,4H)<br>4.40 (s,2H)<br>7.02 (m,10H) |
| 11 | piperidinyl-C(O)-CH₂-NH₂ | 172–174 | DMSO-d6<br>4.33 (s,2H)<br>7.42 (m,3H)<br>8.21 (s,1H) |
| 12 | cyclohexyl-NH-C(O)-CH₂Cl | 114–116 | DMSO-d6<br>1.39 (m,5H)<br>1.80 (m,4H)<br>3.66 (s,2H)<br>4.16 (s,2H)<br>8.25 (d,1H) |
| 13 | PhCH₂-NH-C(O)-CH₂Cl | 133–135 | DMSO-d6<br>3.99 (s,2H)<br>4.16 (d,2H)<br>7.16 (m,5H)<br>8.62 (s,1H) |

B—PREPARATION EXAMPLE OF COMPOUNDS OF FORMULA (II)

Preparation of N-(2,6-Dimethylphenyl)-3-aminopropanamide

A three-necked flask is charged with 400 ml of DMF, 100 g of N-(2,6-dimethylphenyl)-3-chloropropanamide and 95.7 g of potassium phthalimide. After 3 h of stirring at reflux, the reaction medium is cooled to room temperature and 600 ml of water are added. Stirring is continued for 1.5 h. The precipitate formed is filtered off with suction and washed with water. 140 g of white crystals (m.p.>260° C.) are obtained.

The crystals are charged to a three-necked flask with 800 ml of 95° ethanol and 23.7 g of hydrazine monohydrate. After 3 h of stirring at reflux, 39 ml of concentrated hydrochloric acid are added and stirring is continued for 1 h. The precipitate formed is filtered off, and washed with ethanol and the ethanolic phases are concentrated. The crude product obtained is taken up in water; the insoluble material remaining is filtered off and the aqueous phase is concentrated to give 108 g of a cream-white solid.

m.p.=239–241° C. $^1$H NMR (DMSO-d6, 200 MHz): 2.22 (s,6H); 2.44 (t,2H); 2.88 (t,2H); 7.07 (s,3H); 9.50 (s,1H).

The formulae and characteristics of compounds of formula (II) have been collated in Table 2.

TABLE 2

| Compound | Structure | m.p. in ° C. (Köfler) | ¹H NMR 200 MHz δ ppm |
|---|---|---|---|
| 1 | 2,6-dimethylphenyl-NH-CO-CH₂-NH₂ | >260 (HCl) lit.: 296 | DMSO-d6<br>2.15 (d,6H)<br>3.90 (d,2H)<br>7.12 (s,3H)<br>8.40 (s,3H)<br>10.15 (s,1H) |
| 2 | 2,6-diisopropylphenyl-NH-CO-CH₂-NH₂ | 118–120 | DMSO-d6<br>0.88 (s,12H)<br>2.77 (m,2H)<br>3.11 (s,2H)<br>6.92 (m,3H)<br>9.07 (s,1H) |
| 3 | 2,6-bis(methylthio)-4-(methylthio)-6-methylpyridin-3-yl-NH-CO-CH₂-NH₂ | 132–134 | DMSO-d6<br>2.40 (s,6H)<br>2.48 (s,3H)<br>3.34 (s,3H)<br>4.26 (s,3H)<br>6.90 (s,1H) |
| 4 | 2,6-dimethylphenyl-NH-CO-CH₂CH₂-NH₂ | 239–241 (HCl) lit.: 239–240 | DMSO-d6<br>2.22 (s,6H)<br>2.44 (t,2H)<br>2.88 (t,2H)<br>7.07 (s,3H)<br>9.50 (s,1H) |

| Compound | Structure | m.p. in ° C. (Köfler) | ¹H NMR 200 MHz δ ppm |
|---|---|---|---|
| 5 | 2,6-dimethylphenyl-NH-CO-CH(CH₃)-NH₂ | 73–75 | DMSO-d6<br>1.25 (d,3H)<br>2.13 (s,6H)<br>3.50 (m,3H)<br>7.00 (s,3H) |
| 6 | 2,4,6-trimethylphenyl-NH-CO-CH₂-NH₂ | 119–121 | DMSO-d6<br>2.09 (s,6H)<br>2.18 (s,3H)<br>3.28 (s,2H)<br>6.87 (s,2H) |
| 7 | 2,6-dimethylphenyl-NH-CO-CH(NH₂)-CH(CH₃)-CH₂CH₃ | 74–76 | DMSO-d6<br>1.04 (t,3H)<br>1.20 (d,3H)<br>1.30 (m,1H)<br>1.78 (m,3H)<br>2.25 (s,6H)<br>3.35 (d,1H)<br>7.13 (s,3H)<br>9.40 (s,1H) |

TABLE 2-continued

| | | | |
|---|---|---|---|
| 8 | 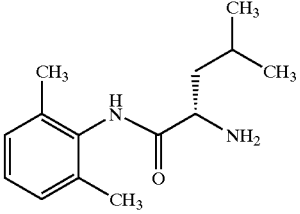 | oil | DMSO-d6<br>1.0 (t,6H)<br>1.63 (m,3H)<br>2.21 (s,6H)<br>3.45 (m,1H)<br>7.12 (s,3H) |
| 9 | 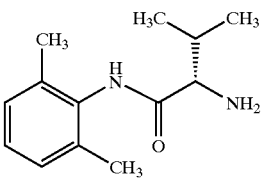 | 71–73 | DMSO-d6<br>0.90 (d,3H)<br>1.05 (d,3H)<br>2.04 (m,1H)<br>2.25 (s,6H)<br>3.27 (d,1H)<br>7.03 (s,3H) |
| 10 | 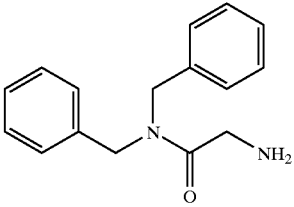 | oil | DMSO-d6<br>3.00 (s,2H)<br>3.54 (s,2H)<br>4.54 (d,4H)<br>7.33 (n,10H) |
| 11 | 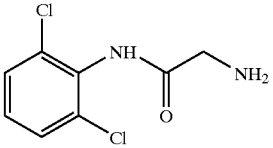 | 108–110 | DMSO-d6<br>3.57 (s,2H)<br>4.69 (s,3H)<br>7.51 (t,1H)<br>7.75 (d,2H) |
| 12 | 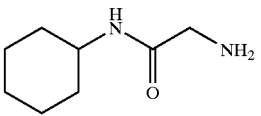 | 89–91 | DMSO-d6<br>1.47 (t,5H)<br>1.91 (m,5H)<br>3.24 (s,2H)<br>3.77 (m,1H)<br>7.83 (d,1H) |
| 13 | 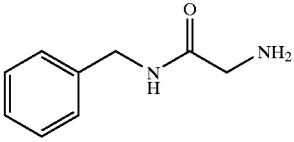 | oil | DMSO-d6<br>2.69 (s,2H)<br>3.34 (s,2H)<br>4.50 (d,2H)<br>7.49 (m,5H)<br>8.52 (s,1H) |

C—PREPARATION EXAMPLE OF COMPOUNDS OF FORMULA (II)

Preparation of N-(2,6-Dimethylphenyl)-2-methylamino-acetamide

A closed stainless-steel reactor is charged with 80 g of N-(2,6-dimethylphenyl)-2-chloro-acetamide and 600 ml of a 40% aqueous methylamine solution. The mixture is heated with stirring at 80° C. for 4 h and then concentrated under vacuum. The crude product is taken up in water and washed with dichloromethane. The aqueous solution is basified using sodium hydroxide solution and extracted with dichloromethane. The organic, phase is dried over sodium sulphate and concentrated to give 60 g of a colourless oil.

$^1$H NMR (DMSO-d6, 200 MHz): 2.15 (s,6H); 2.44 (s,3H); 3.50 (s,2H); 6.50 (s,1H); 7.70 (s,3H); 9.58 (s,1H).

The formulae and characteristics of compounds have been collated in Table 3.

TABLE 3

| Compound | Structure | m.p. in °C (Kofler) | ¹H NMR 200 MHz δ ppm |
|---|---|---|---|
| 1 | 2,6-dimethylphenyl-NH-C(O)-CH₂-NH-CH₃ | oil | DMSO-d6<br>2.15 (s,6H)<br>2.44 (s,3H)<br>3.50 (s,2H)<br>6.50 (s,1H)<br>7.07 (s,3H)<br>9.58 (s,1H) |
| 2 | H₂N-C(O)-CH₂-NH-CH₃ | oil | 13C NMR 50 MHz δ ppm<br>DMSO-d6<br>34.80 CH3-N<br>54.28 CH2<br>180.09 C=O |

D—PREPARATION EXAMPLE OF COMPOUNDS OF FORMULA (I)

Preparation of 2-Aminoiminomethylamino-N-(cyclohexyl)acetamide

A round-bottomed flask is charged with 15 g of 2-amino-N-(cyclohexyl)-acetamide, 14,6 g 1-aminoimino-mehtylpyrazole hydrochloride and 100 ml of dioxane. After 18 h stirring at reflux, the reaction medium is cooled to room temperature and precipitate which has formed is filtered off with suction. 16 g of a white solid are obtained.

m.p.=232–234° C. ¹H NMR (DMSO-d6, 200 MHz): 1.19 (m,5H); 1.62 (m,5H); 3.46 (m,1H); 3.78 (d,2H); 7.21 (s,4H); 7.68.

The formulae and characteristics of compounds of formula (I) have been collated in Table 4.

TABLE 4

| Compound | Structure | m.p. in °C (Kofler) | ¹H NMR 200 MHz d ppm |
|---|---|---|---|
| 1 | 2,6-dimethylphenyl-NH-C(O)-CH₂-NH-C(NH)-NH₂ | 255–257 (0.5 H₂SO₄) | DMSO-d6<br>2.25 (s,6H)<br>4.25 (s,2H)<br>7.15 (s,3H)<br>7.95 (s,3H)<br>8.35 (s,1H)<br>10.10 (s,1H) |
| 2 | 2,6-diisopropylphenyl-NH-C(O)-CH₂-NH-C(NH)-NH₂ | 260–262 (HCl) | DMSO-d6<br>1.31 (d,12H)<br>3.22 (m,2H)<br>4.35 (s,2H)<br>7.37 (m,3H)<br>7.64 (s,2H)<br>7.91 (s,2H)<br>9.91 (s,1H) |
| 3 | 4-(methylthio)-6-methyl-2-(methylthio)pyridin-3-yl-NH-C(O)-CH₂-NH-C(NH)-NH₂ | 249–251 (HCl) | DMSO-d6<br>2.40 (3s,9H)<br>4.15 (s,2H)<br>6.92 (s,1H)<br>7.44 (s,3H)<br>7.74 (s,1H)<br>9.88 (s,1H) |
| 4 | 2,6-dimethylphenyl-NH-C(O)-CH₂-CH₂-NH-C(NH)-NH₂ | 223–225 | DMSO-d6<br>2.16 (s,6H)<br>2.65 (t,2H)<br>3.50 (t,2H)<br>7.08 (s,3H)<br>7.31 (m,3H)<br>7.85 (s,2H)<br>9.69 (s,1H) |

TABLE 4-continued

| Compound | Structure | m.p. in °C. (Köfler) | ¹H NMR 200 MHz δ ppm |
|---|---|---|---|
| 5 | (2,6-dimethylphenyl)-NH-C(=O)-CH2-N(CH3)-C(=NH)NH2 | 227–229 (HCl) | DMSO-d6<br>2.05 (s,6H)<br>2.88 (s,3H)<br>4.25 (s,2H)<br>6.95 (s,4H)<br>9.68 (s,1H) |
| 6 | (2,6-dimethylphenyl)-NH-C(=O)-CH(CH3)-NH-C(=NH)NH2 | 159–161 (HCl) | DMSO-d6<br>1.53 (d,3H)<br>2.27 (s,6H)<br>7.20 (s,3H)<br>4.85 (m,1H)<br>7.20 (d,1H)<br>7.55 (s,2H)<br>8.10 (d,1H)<br>10.00 (s,1H) |
| 7 | (2,4,6-trimethylphenyl)-NH-C(=O)-CH2-NH-C(=NH)NH2 | >260 (HCl) | DMSO-d6<br>2.15 (s,6H)<br>2.24 (s,3H)<br>4.18 (d,2H)<br>6.90 (s,2H)<br>7.50 (s,2H)<br>7.87 (s,1H)<br>9.70 (s,1H) |
| 8 | (2,6-dimethylphenyl)-N=C(O-)-CH(sec-Bu)-NH-C(=NH)NH2 | amorphous (HCl) | DMSO-d6<br>1.0 (m,6H)<br>1.30 (m,1H)<br>1.50 (m,1H)<br>1.93 (m,H)<br>2.25 (s,6H)<br>4.60 (d,1H)<br>7.17 (s,3H)<br>7.95 (s,2H)<br>9.55 (s,1H) |
| 9 | (2,6-dimethylphenyl)-NH-C(=O)-CH(iBu)-NH-C(=NH)NH2 | amorphous (HCl) | DMSO-d6<br>1.05 (d,6H)<br>1.69 (m,3H)<br>2.18 (s,6H)<br>4.87 (s,1H)<br>7.15 (s,3H)<br>8.02 (s,2H)<br>10.18 (s,1H) |
| 10 | (2,6-dimethylphenyl)-N=C(O-)-CH(iPr)-N(CH3)-C(=NH)NH2 | amorphous (HCl) | DMSO-d6<br>1.0 (m,6H)<br>2.25 (m,7H)<br>4.57 (t,1H)<br>7.12 (s,3H)<br>8.08 (s,2H)<br>10.20 (s,1H) |
| 11 | (PhCH2)2N-C(=O)-CH2-NH-C(=NH)NH2 | 217–219 (HCl) | DMSO-d6<br>4.51 (s,2H)<br>4.68 (s,2H)<br>7.58 (m,15H) |

TABLE 4-continued

| | | | |
|---|---|---|---|
| 12 | 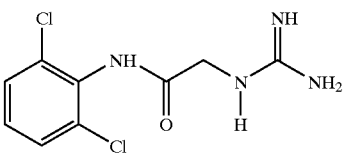 | 181–183 (HCl) | DMSO-d6<br>4.30 (d,2H)<br>7.52 (m,3H)<br>7.91 (s,1H)<br>10.45 (s,1H) |
| 13 | 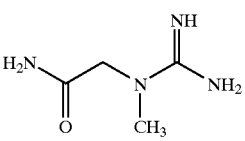 | >250 (HCl) | DMSO-d6<br>3.00 (s,3H)<br>3.52 (s,5H)<br>3.76 (s,2H) |
| 14 | 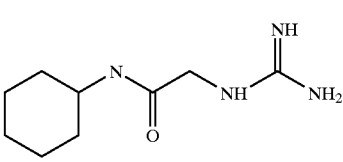 | 232–234 (HCl) | DMSO-d6<br>1.19 (m,5H)<br>1.62 (m,5H)<br>3.46 (m,1H)<br>3.78 (d,2H)<br>7.21 (s,4H)<br>7.68 (t,1H)<br>8.16 (d,1H) |
| 15 | 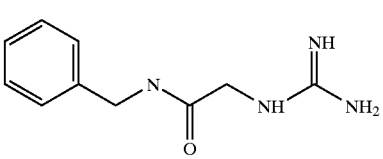 | 144–146 (HCl) | DMSO-d6<br>4.04 (d,2H)<br>4.42 (d,2H)<br>7.44 (m,9H)<br>7.79 (t,1H)<br>8.89 (t,1H) |

The results of pharmacological studies will be given below.

Study of the Antidiabetic Activity in the Nostz Rat

The antidiabetic activity of the compounds of formula (I) was determined orally on an experimental model of non-insulin-dependent diabetes induced in the rat using streptozotocin.

The model of non-insulin-dependent diabetes is obtained in rats by neonatal injection (on the day of birth) of streptozotocin.

The diabetic rats used are 8 weeks old. The animals are kept from the day of their birth to the day of the experiment in an animal house at a regulated temperature of from 21 to 22° C. and are subjected to a fixed cycle of light (from 7.00 am to 7.00 pm) and darkness (from 7.00 pm to 7.00 am). Their diet consisted of a maintenance diet; water and food were provided ad libitum, except for the 2 hours fasting prior to the tests in which food is withdrawn (post-absorptive state).

The rats are treated orally for one (d1) or four (d4) days with the test product. Two hours after the final administration of the product and 30 minutes after anaesthesia of the animals with sodium pentobarbital (Nembutalo®), 300 ml of blood is sampled from the end of the tail.

Results obtained are collated, by way of example, in Table 5. These results demonstrate the efficacy of the compounds of formula (I) in reducing glycaemia in diabetic animals. These results are expressed as a percentage change in glycaemia on d1 and d4 (number of days of treatment) relative to d0 (before treatment).

TABLE 5

| | 20 mg/kg/d | | 200 mg/kg/d | |
|---|---|---|---|---|
| | d1 | d4 | d1 | d4 |
| Example | | | | |
| 1 | −3 | −7 | −20 | −24 |
| 3 | +7 | −7 | −5 | −4 |
| 4 | −1 | −11 | −13 | −15 |
| 5 | −2 | −7 | −16 | −25 |
| Compounds | | | | |
| 6 | +8 | −3 | −4 | −18 |
| 7 | −9 | −9 | −3 | −10 |
| 8 | −11 | −14 | −8 | −10 |
| 9 | −4 | −15 | +7 | −4 |
| 10 | −13 | −15 | −3 | −16 |
| 11 | −14 | −9 | −3 | −16 |
| 12 | −9 | −13 | −14 | −27 |

Study of the Antiglycoxidation Activity

The compounds (I) are also capable of inhibiting the so-called Maillard reactions by means of a "scavenging" effect on α-dicarbonyl derivatives such as glyoxal—this is the antiglycation effect. This inhibitory effect on the Maillard reaction by the compounds of formula (I) was studied in vitro by assaying the ketamines ("fructoamines") produced during the incubation of albumin with methylglyoxal in the presence or absence of a compound of formula (I).

A 6.6 mg/ml solution of bovine albumin in 0.2 M phosphate buffer pH 7.4 is incubated with 1 mM methylglyoxal in the presence or absence of a compound according to the invention at a concentration of 1 mM. The incubation is carried out under sterile conditions at 37° C. for 6 days. At the end of the incubation period, the amount of ketamines is measured with a commercially available fructoamine assay kit (kit "FRA", product reference: 0757055, Roche S. A. products) in accordance with the manufacturer's instructions. Under these experimental conditions, the level of fructoamine following incubation of albumin with methylglyoxal in the presence of a compound of formula (i) is from 30 to 50% lower than that observed when albumin is incubated with methylglyoxal in the absence of the compound of formula (I).

What is claimed is:

1. A compound which is

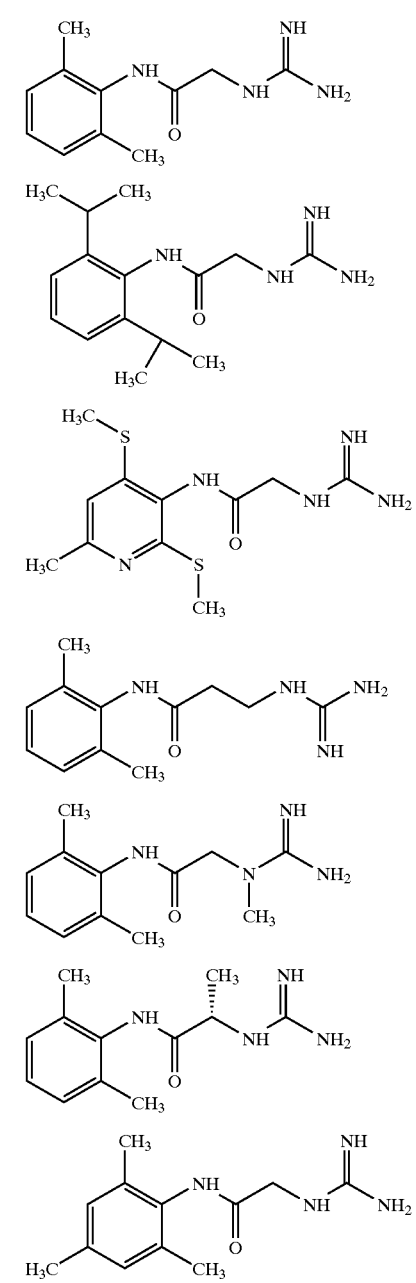

-continued

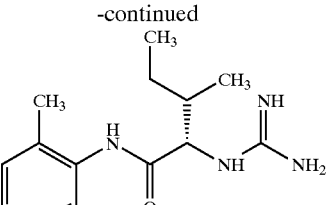

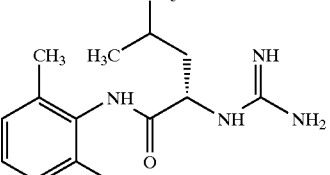

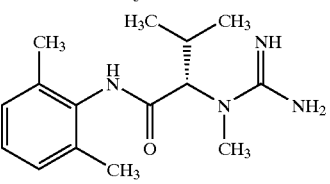

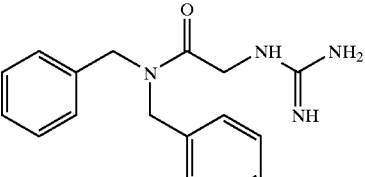

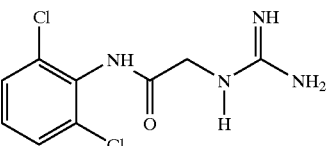

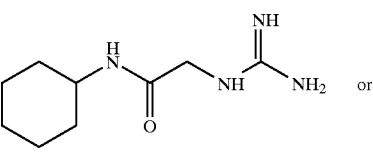

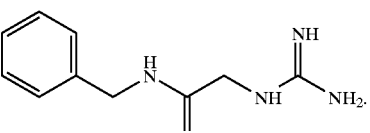

or

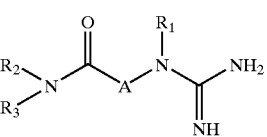

2. A pharmacuetical composition comprising a compound according to claim 1 and a pharmacuetical acceptable excipient.

3. A method for treating a pathology associated with insulin resistance syndrome, comprising administering to a patient in need thereof an effective amount of a composition of claim 2.

4. A process for preparing a compound of formula (I):

(I)

$$R_2\text{-}N(R_3)\text{-}C(=O)\text{-}A\text{-}N(R_1)\text{-}C(=NH)\text{-}NH_2$$

in which:

$R^1$ is H or
a $C_1$–$C_{20}$ alkyl which is unsubstituted or substituted by one or more amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups, R is a $C_3$–$C_8$ cycloalkyl which is unsubstituted or substituted by one or more amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups, a $C_6$–$C_{14}$ aryl which is unsubstituted or substituted by one or more
amino, hydroxyl, halogen, $C_1$–$C_5$ alkyl, $C_1$–$C_5$ alkoxy,
$C_1$–$C_5$ alkylthio, $C_1$–$C_5$ alkylamino, trifluoromethyl or cyano groups, or a $C_1$–$C_{13}$ heteroaryl which contains one or more heteroatoms selected from the group consisting of N, O and S, and which is unsubstituted or substituted by one or more
amino, hydroxyl, halogen, $C_1$–$C_5$ alkyl, $C_1$–$C_5$ alkoxy, $C_1$–$C_5$ alkylthio, $C_1$–$C_5$ alkylamino, trifluoromethyl or cyano groups, wherein a nitrogen atom is optionally substituted with a $C_6$–$C_{14}$ aryl, $C_6$–$C_{14}$ acyl or $C_1$–$C_5$ alkyl group, $R_3$ is H,
a $C_3$–$C_8$ cycloalkyl which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups, a $C_3$–$C_8$ heterocycloalkyl which contains one or more heteroatoms selected from the group consisting of N, O and S, and which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups,
wherein a nitrogen atom is optionally substituted with a $C_6$–$C_{14}$ aryl, $C_6$–$C_{14}$ acyl or $C_1$–$C_5$ alkyl group, a $C_6$–$C_{14}$ aryl which is unsubstituted or substituted by one or more
amino, hydroxyl, halogen, $C_1$–$C_5$ alkyl, $C_1$–$C_5$ alkoxy, $C_1$–$C_5$ alkylthio, $C_1$–$C_5$ alkylamino, trifluoromethyl or cyano groups,
a $C_1$–$C_{13}$ heteroaryl which contains one or more heteroatoms selected from the group consisting of N, O and S, and which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino, trifluoromethyl or cyano groups,
wherein a nitrogen atom is optionally substituted with a $C_6$–$C_{14}$ aryl, $C_6$–$C_{14}$ acyl or $C_1$–$C_5$ alkyl group, or a $C_6$–$C_{14}$ aryl-$C_1$–$C_5$ alkyl which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino, trifluoromethyl or cyano groups, and A is —$CH_2$—$CH_2$—, or —$CHR_4$—, wherein
$R_4$ is H,
a $C_1$–$C_{20}$ alkyl which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups,
a $C_3$–$C_8$ cycloalkyl which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups,
a $C_3$–$C_8$ heterocycloalkyl which contains one or more heteroatoms selected from the group consisting of N, O and S, and which is unsubstituted or substituted by one or more
amino, hydroxyl, $C_1$–$C_5$ alkyl, $C_1$–$C_5$ alkoxy, $C_1$–$C_5$ alkylthio, $C_1$–$C_5$ alkylamino or trifluoromethyl groups,
wherein a nitrogen atom is optionally substituted with a $C_6$–$C_{14}$ aryl, $C_6$–$C_{14}$ acyl or $C_1$–$C_5$ alkyl group;

or a solvate or a pharmaceutically acceptable salt thereof, with the exception of the compound of formula (I) in which $R_1$=H, $R_2$=phenyl and $R_3$=H, comprising reacting a compound of formula (U)

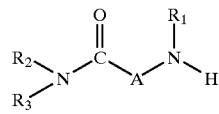

(II)

with a compound of formula (II) or (IV)

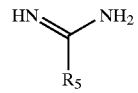

(III)

or

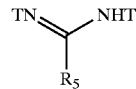

(IV)

in which
$R_5$ is —$SCH_3$, pyrazolyl —$SOH_3H$, and
T is a tert-butyloxycarbonyl or benzyloxycarbonyl protective group.

* * * * *

UNITED STATES PATENT AND TRADEMARK OFFICE
CERTIFICATE OF CORRECTION

PATENT NO. : 6,518,458 B1 Page 1 of 1
DATED : February 11, 2003
INVENTOR(S) : Gerard Moinet et al.

It is certified that error appears in the above-identified patent and that said Letters Patent is hereby corrected as shown below:

Title page,
Item [54], reads "(AMINOIMINOMETHYL)" should read
-- ((AMINOIMINOMETHYL) --; and "ALKANE-CARBOXAMIDES" should read
-- ALKANECARBOXAMIDES --

Column 20,
Line 52, reads "pharmacuetical composition" should read -- pharmaceutical composition --
Line 53, reads "pharmacuetical acceptable" should read -- pharmaceutically acceptable --

Column 22,
Line 29, reads "formula (U)" should read -- formula (II) --
Line 37, reads "formula (II) or (IV)" should read -- formula (III) or (IV) --
Line 52, reads "pyrazolyl" should read -- pyrazolyl or --

Signed and Sealed this

Twenty-third Day of September, 2003

JAMES E. ROGAN
*Director of the United States Patent and Trademark Office*